United States Patent [19]

Meiklejohn

[11] 4,245,506
[45] Jan. 20, 1981

[54] POROUS MEMBRANE HUMIDITY SENSOR

[75] Inventor: William H. Meiklejohn, Scotia, N.Y.

[73] Assignee: General Electric Company, Schenectady, N.Y.

[21] Appl. No.: 77,115

[22] Filed: Sep. 19, 1979

[51] Int. Cl.$^3$ .................. G01R 27/00; G01W 1/11; H01L 49/02
[52] U.S. Cl. .................. 73/336; 73/336.5; 338/35
[58] Field of Search .............. 73/335, 336, 337, 336.5; 338/35

[56] References Cited

U.S. PATENT DOCUMENTS

| | | | |
|---|---|---|---|
| 2,526,636 | 10/1950 | Colman | 73/335 |
| 3,440,372 | 4/1969 | Cecil | 338/35 X |
| 3,713,921 | 1/1973 | Fleischer et al. | 156/2 |
| 4,083,249 | 4/1978 | Gerber | 73/336.5 |

OTHER PUBLICATIONS

Publication: "Electric Hygrometer" by W. H. Meiklejohn (Jul. 1958) Transactions of the AIEE, vol. 77, Part 1, TK 1A6.

*Primary Examiner*—Daniel M. Yasich
*Attorney, Agent, or Firm*—Donald R. Campbell; Marvin Snyder; James C. Davis

[57] ABSTRACT

An improved sensor which responds to varying relative humidity by a change in impedance does not fail at 95-100 percent relative humidity. A microporous glass membrane or irradiated-and-etched plastic membrane contains a salt in its pores and has conductive coatings on both surfaces and hydrophobic films on the conductive coatings. At high humidities the pore fills with water and forms a bulge on the end of the pore because water will not wet the hydrophobic film. With proper choice of the pore radius no salt solution spills out.

7 Claims, 7 Drawing Figures

U.S. Patent  Jan. 20, 1981  4,245,506
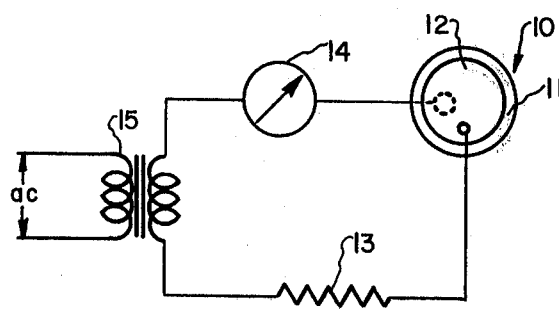
Fig.1
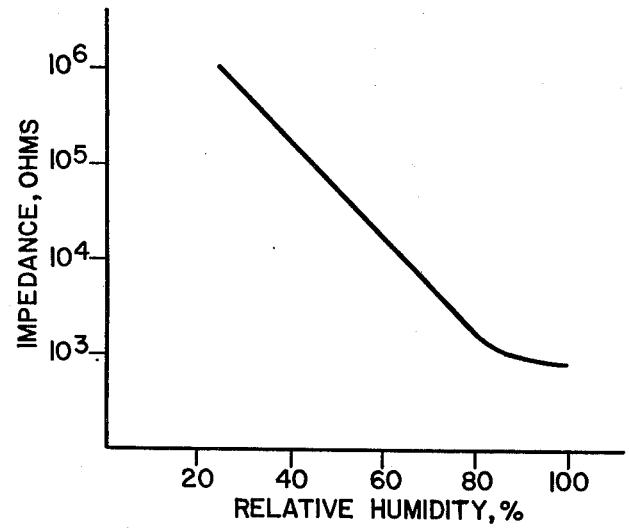
Fig.2
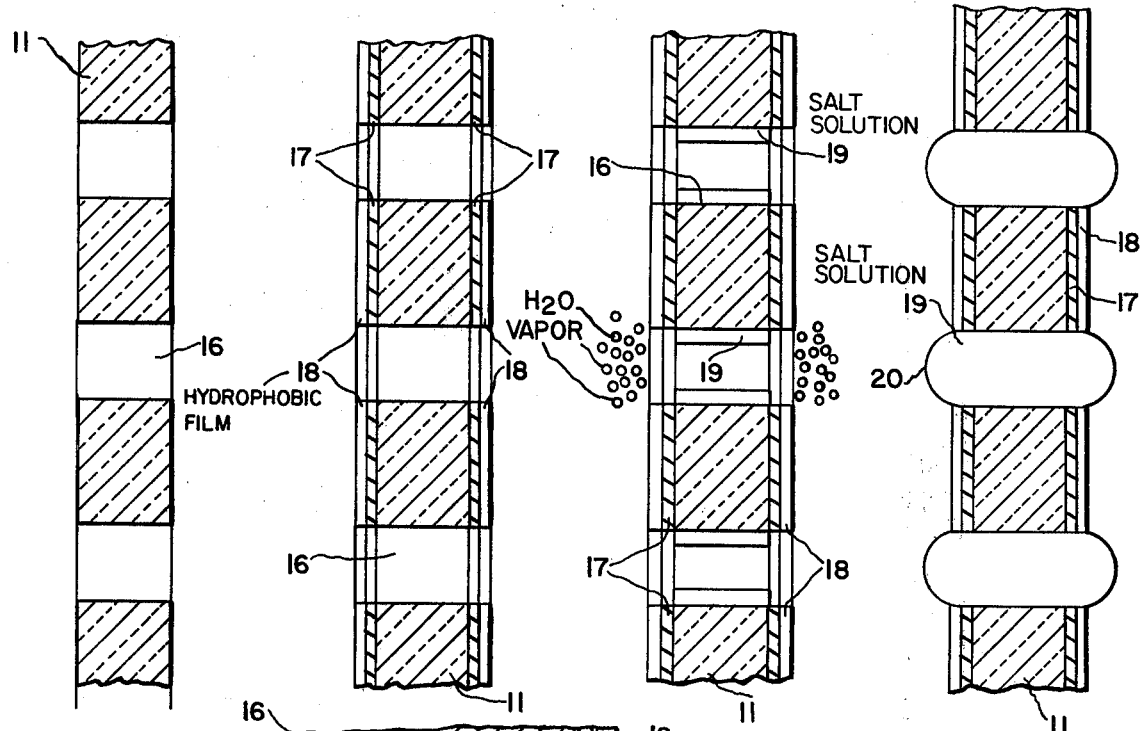
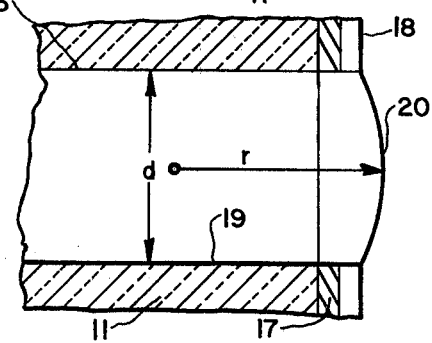
Fig.7

POROUS MEMBRANE HUMIDITY SENSOR

BACKGROUND OF THE INVENTION

This invention relates to humidity sensing devices and especially to an improved electric hygrometer which measures over the full useful range up to 100 percent relative humidity.

Present humidity sensors based upon electrolytic conduction through a salt solution fail after exposure to 95 percent or greater humidity. The reason for this is lack of containment of the salt solution. One type has a bifilar winding on a rod that is coated with lithium chloride; the solution drips off the coated rod at these high humidities because the solution is tending toward infinite dilution and infinite volume in order to attain the vapor pressure of pure water. Another type consists of a porous membrane containing the salt in its pores and is described by the inventor in "Electric Hygrometer", Transactions of the AIEE, Vol. 77, Part I, Communication and Electronics, July 1958, pp. 302–305. This invention is an improvement over the foregoing.

SUMMARY OF THE INVENTION

An improved humidity sensing device has a microporous glass or plastic membrane containing a hygroscopic salt such as lithium chloride in its pores. On both major surfaces of the membrane are porous conductive coatings which serve as electrodes, and hydrophobic films are over the conductive coatings. Upon applying an alternating voltage between the electrodes, electrolytic conduction takes place and the sensor responds to varying relative humidity by a change in its impedance. This structure provides containment of the salt solution even at high relative humidities above 95 percent when the individual pores are filled with water. The solution forms a bulge on the end of the pore because the solution does not wet the hydrophobic film on the surface. It is known that the vapor pressure of a curved surface is greater than the vapor pressure of a flat surface. Assuming that the pore radius is sufficiently small and is much less than the radius of the curved solution surface at 100 percent relative humidity, the pore ceases taking on water vapor and does not spill out and cause a failure at high humidities. For example, if the pore radius is less than 0.3 $\mu$m, the vapor pressure of 0.1 normal lithium chloride solution in the pore will equal the vapor pressure of pure water. The bulge stops growing and the salt solution is contained.

A porous glass membrane 5–20 mils thick with a pore diameter of 40 Å–100 Å exhibits good stability and a fast response time. An irradiated-and-etched plastic membrane with a thickness of about 10 $\mu$m and a pore diameter of about 0.2 $\mu$m (2000 Å) is also suitable. Other electrolytes are zinc chloride, lithium bromide, and a combination of lithium chloride and lithium bromide.

BRIEF DESCRIPTION OF THE DRAWINGS

FIG. 1 is a schematic diagram of the electrical humidity sensor;

FIG. 2 is a plot of impedance in ohms vs. relative humidity for a porous plastic sensor;

FIGS. 3 and 4 are partial cross sections of a porous glass sensor showing steps in its fabrication;

FIGS. 5 and 6 are partial cross sections of the device illustrating the salt in the pores at low relative humidity and at high relative humidity; and FIG. 7 is an enlarged partial section of one pore filled with electrolyte at 100 percent relative humidity.

DESCRIPTION OF THE PREFERRED EMBODIMENTS

Humidity sensor or hygrometer 10 in FIG. 1 is comprised of a porous glass or plastic membrane 11 having a large number of pores of relatively small diameter which extend completely through the membrane. The pores contain a hygroscopic salt solution such as lithium or zinc chloride. Porous metal electrodes 12 on the surfaces of the membrane are connected in series circuit relationship with a limiting resistor 13 and a milliammeter 14. A transformer 15 connected to an ac source supplies 24 volt alternating current to the circuit and electrolytic conduction takes place between the porous metal electrodes. The resistance of the hygrometer varies with the relative humidity (RH) or water vapor pressure in the air. The salt solution in the pores absorbs more water when an increase in relative humidity occurs; the resistance of the solution in the pore decreases and more current flows. Similarly, a decrease in current is obtained with a decrease in relative humidity. A hydrophobic film on metal electrodes 12, which does not extend in the pores, prevents spilling of solution out of the pores at high relative humidities above 95 percent. On a semilogarithmic scale, as shown in FIG. 2, the variation of impedance with relative humidity is approximately linear. The sensor measures relative humidity over a full useful range of 10–100 percent relative humidity.

Referring to FIGS. 3 and 4, porous glass membrane 11 is known as Corning Thirsty Glass and occurs in a stage of the process of making Vycor ® Brand 96 percent silica glasses. A special borosilicate glass is separated into two contiguous phases by heating. One phase is mainly silica, $SiO_2$, and the second phase is mainly borate, $B_2O_3$. The borate rich phase is leached out by a weak sodium hydroxide solution. Porous glass membrane 11 is about 10 mils thick and pores 16 are 40 Å–100 Å in diameter. A thin film of gold 17 is evaporated onto the major surfaces of the porous glass and serve as the electrodes. These conductive coatings are porous or vapor-permeable and may be 300 Å of gold on 50 Å of chromium to reduce the surface resistivity and realize better adhesion to glass. Hydrophobic films 18 are deposited on both conductive coatings 17. One liquid hydrophobic material that is readily available is Nye Bar, sold by William F. Nye, Inc., New Bedford, Mass. This is a clear, mobile solution of an oleophobic hydrophobic fluorochemical polymer in "Freon" TF. When applied to clean surfaces, the solution dries to an extremely thin, transparent film possessing excellent antimigration properties against low energy liquids. The unique antimigration properties are due primarily to the extremely low surface energy exhibited by the polymer film itself. Also important are the insolubility in most nonfluorinated solvents, and the ability to form a clear and uniform film on a variety of substrates. This film has excellent repellency to aqueous solutions. Dip-coating the hydrophobic film applies it to the conductive coatings without getting it into the pores. An evaporation process would also be a good procedure.

The response time of the sensor is faster for thin porous membrane materials; also, the larger the diameter of the pore, the faster is the response time. Porous glass sensors are stable and have a satisfactory response time for most applications if the porous membrane is 20 mils thick or less. The response time of 5 or 10 mil glass is much faster, of course, than 20 mil glass. An irradiated-and-etched plastic porous membrane is available which has a much shorter response time partly due to the larger pore size and partly due to a thinner membrane. These membranes or filters consist of a ½ mil thick polycarbonate film which has been exposed to heavy particle radiation to produce very small damaged tracks which are subsequently etched with a sodium hydroxide solution. The filters can be purchased from Nuclepore Corp., Pleasanton, Calif., and disk membranes without center holes are available in 16 pore sizes from 12 μm down to 0.015 μm. Code number NO20 has a pore diameter of 0.2 μm, a nominal thickness of 10 μm, and a pore density of $3 \times 10^8$ pores/cm². Porous plastic sensors were made by filtering a 0.1 normal lithium chloride solution through a Nuclepore filter. The filter was clamped in a two part funnel and the lithium chloride solution was pulled through the filter by applying a vacuum to the lower end of the funnel. After treatment with lithium chloride, a 300 Å layer of gold was evaporated on each side of the filter. The gold surface was then coated with a hydrophobic film, and the sensor was mounted between two gold plated bronze rings. One problem with the polycarbonate membrane material is that it is subject to hydrolysis at high humidities and is unstable. An irradiated-and-etched plastic membrane of PPO ® oxidatively coupled polymeric material would be stable and appears to be a better choice.

FIGS. 5 and 6 show the salt in the pores of the porous glass sensor under low and high relative humidity conditions. At 20 percent relative humidity, for instance, the concentration of the lithium chloride solution increases and there is a thin film of salt solution 19 on the surfaces of the pores. Water molecules go into and out of the pores until the water vapor pressure of lithium chloride solution in the pore equals the water vapor pressure of the surrounding air. At this point of equilibrium, the cross-sectional area of lithium chloride solution in the pore will increase as the water vapor pressure in the surrounding air increases. As a result of the increased cross-sectional area of lithium chloride solution with increasing ambient water vapor pressure, the resistance of the sensor (between metal electrodes 17) will decrease. Lithium chloride is chosen for the salt since it is highest in the electromotive series and above hydrogen. Hence, hydrogen and oxygen are plated out at each electrode during a cycle. Recombination of the hydrogen and oxygen prevents the explusion of liquid from the pores.

At approximately 100 percent relative humidity, the pore fills up with water vapor and salt solution 19 tends to spill out. It is known that the vapor pressure of a curved surface is greater than the vapor pressure of a flat surface. Hydrophobic film 18 causes a curved surface at the pore exit by preventing wetting of the surface. Calculations show that if the pore radius is less than 0.3 μm, the vapor pressure of 0.1 N lithium chloride solution in the pore will equal the vapor pressure of pure water. Therefore, the pore will cease taking on more water vapor and will not spill out of the pore and cause a failure at high humidities.

FIG. 7 is referred to in the calculation for the maximum permissible pore radius (d/2) to contain salt solution without loss. Let $p_c$=vapor pressure of the curved surface, $p_f$=vapor pressure of a flat surface, $p_w$=100 percent RH. The ratio of the vapor pressure of a curved surface to that of a flat surface is:

$$\frac{p_c}{p_f} = e^{\frac{\alpha}{r}} = 1 + \frac{\alpha}{r} + \ldots = 1 + \frac{10^{-7}}{r},$$

where r=radius of curved surface and $\alpha=2 \gamma v/kT$, where $\gamma$ is the surface tension, v is the molecular volume of water, k is Boltzman's constant, and T is the absolute temperature. For a flat surface $p_f=0.9969 \, p_w$ (0.1 N LiCl solution);

or, $p_w/p_f = 1/0.9969$

∴ for $p_c = p_w$ $1 + (0^{-7}/r) = 1/0.9969$ hence: $r = 0.3 \times 10^{-4}$ cm = 0.3 μm The curved surface of a 0.1 N lithium chloride solution will match the vapor pressure of a flat surface of pure water if $r \leq 0.3$ μm. If the radius of the curved surface has the maximum value of 0.3 μm, the pore radius can be no greater than 0.3 μm because a droplet would form and drop off. In practice the pore radius is chosen to be substantially less than 0.3 μm, for example 0.1 μm. To prevent loss of salt solution there is a hydrophobic film on the sensor surface and the pore radius is less than the radius of the curved salt solution surface which bulges out beyond the hydrophobic film at 100 percent relative humidity.

Explaining this another way, water will form a bulge 20 at the end of the pore because the water or salt solution will not wet the hydrophobic film on the surface. The evaporation rate of the water on the surface of the bulge will increase as the bulge grows because the evaporation rate is inversely proportional to the radius of curvature. When the evaporation rate equals the condensation rate the bulge will stop growing. The pore diameter is sufficiently small that this occurs before water spills out of the pore.

Other salts may be used in the pores such as zinc chloride, lithium bromide, and a combination of lithium chloride and lithium bromide. The range of resistance variation with relative humidity is governed by the vapor pressure characteristics of the salt solution. The metal electrodes alternatively may be chromium, palladium, or nichrome, or combinations of these. The response of the improved porous membrane sensors to a change in humidity is fast enough (on the order of several seconds or less) to be used in household appliances such as room air conditioners, dryers, and microwave ovens.

While the invention has been particularly shown and described with reference to several preferred embodiments thereof, it will be understood by those skilled in the art that the foregoing and other hanges in form and details may be made therein without departing from the spirit and scope of the invention.

The invention claimed is:

1. An improved humidity sensor having an impedance which varies with relative humidity comprising:
    an insulating porous membrane having a large number of pores extending from one major surface of said membrane to the other;
    porous conductive coatings on both major surfaces of said membrane;
    hydrophobic films on both conductive coatings; and a hygroscopic salt solution in said pores which exhibits electrolytic conduction upon applying an alternating voltage between
said conductive coatings;
the radius of said pores being sufficiently small and less than the radius of the curved said solution surface bulging out beyond said hydrophobic films at 100% relative humidity, that said salt solution does not spill out.

2. The humidity sensor of claim 1 wherein said salt solution is selected from the group consisting of lithium chloride, zinc chloride, lithium bromide, and a combination of lithium chloride and lithium bromide.

3. The humidity sensor of claim 2 wherein said porous membrane is an irradiated-and-etched plastic membrane.

4. The humidity sensor of claim 1 wherein said porous membrane is a plastic membrane, said salt solution is lithium chloride, and the diameter of said pores is about 0.2 $\mu$m.

5. An improved humidity sensor having an impedance which varies with relative humidity comprising:

an insulating porous membrane having a large number of pores extending from one major surface of said membrane to the other;
porous metallic coatings on both major surfaces of said membrane;
hydrophobic films on both metallic coatings; and
a dilute hygroscopic salt solution in said pores which exhibits electrolytic conduction upon applying an alternating voltage between said metallic coatings;
the radius of said pores being less than the radius of the curved salt solution surface which bulges out beyond said hydrophobic film at 100 percent relative humidity whereby said salt solution is contained and does not spill out.

6. The humidity sensor of claim 5 wherein said porous membrane is a glass membrane having a thickness of less than 20 mils and said salt solution is lithium chloride.

7. The humidity sensor of claim 5 wherein said porous membrane is an irradiated-and-etched plastic membrane, said salt solution is lithium chloride, and the diameter of said pores is no greater than 0.2 $\mu$m.

* * * * *